(12) United States Patent
Bantz et al.

(10) Patent No.: US 9,470,215 B2
(45) Date of Patent: Oct. 18, 2016

(54) MINIATURIZED SYRINGE PUMP SYSTEM AND MODULES

(75) Inventors: Daniel L. Bantz, Brookline, NH (US);
Paul M. Grippo, Bedford, NH (US);
Donald S. McNeil, Brookline, NH (US); Kenneth D. Wynn, Boylston, MA (US); Angela Tseng, Pepperell, MA (US)

(73) Assignee: Parker-Hannifin Corporation, Cleveland, OH (US)

( * ) Notice: Subject to any disclaimer, the term of this patent is extended or adjusted under 35 U.S.C. 154(b) by 678 days.

(21) Appl. No.: 13/701,853

(22) PCT Filed: Jun. 6, 2011

(86) PCT No.: PCT/US2011/039264
§ 371 (c)(1),
(2), (4) Date: Feb. 7, 2013

(87) PCT Pub. No.: WO2011/153526
PCT Pub. Date: Dec. 8, 2011

(65) Prior Publication Data
US 2013/0129538 A1    May 23, 2013

Related U.S. Application Data

(60) Provisional application No. 61/351,550, filed on Jun. 4, 2010.

(51) Int. Cl.
*F04B 17/03* (2006.01)
*A61M 5/145* (2006.01)
(Continued)

(52) U.S. Cl.
CPC ............ *F04B 17/03* (2013.01); *A61M 5/1452* (2013.01); *A61M 5/1456* (2013.01);
(Continued)

(58) Field of Classification Search
CPC ............ A61M 5/1452; A61M 5/1456; B01L 3/0217; F04B 17/03; F04B 19/006; G01N 35/1072
See application file for complete search history.

(56) References Cited

U.S. PATENT DOCUMENTS

| 4,087,248 A | 5/1978 | Miles |
| 4,424,720 A | 1/1984 | Bucchianeri |

(Continued)

FOREIGN PATENT DOCUMENTS

| EP | 0984284 | 3/2000 |
| EP | 2017477 | 1/2009 |

(Continued)

OTHER PUBLICATIONS

Search report for corresponding International Application No. PCT/US2011/039264, dated Dec. 12, 2011.

*Primary Examiner* — Jill Warden
*Assistant Examiner* — Julie Tavares
(74) *Attorney, Agent, or Firm* — Renner, Otto, Boisselle & Sklar, LLP

(57) ABSTRACT

Provided is a liquid handling device for use in a liquid handling system including a plurality of the liquid handling devices assembled in side-by-side relationship at a center-to-center spacing of X. The device includes a barrel, plunger, motive device and electronics assembled together in an envelope having a front portion including at least the barrel and plunger, and a rear portion including at least a portion of the electronics. The rear portion has a thickness greater than X but no greater than 2X, and the front portion has a thickness no greater than X and is laterally offset relative to a center plane of the envelope, whereby the liquid handling device can be assembled with another reversely oriented liquid handling device at a center-to-center spacing of X and a total combined width no greater than 2X.

20 Claims, 14 Drawing Sheets

(51) Int. Cl.
*B01L 3/02* (2006.01)
*F04B 19/00* (2006.01)
*G01N 35/10* (2006.01)
*G01N 35/00* (2006.01)

(52) U.S. Cl.
CPC .......... *B01L 3/0217* (2013.01); *F04B 19/006* (2013.01); *G01N 35/1072* (2013.01); *B01L 2200/028* (2013.01); *B01L 2300/0861* (2013.01); *G01N 2035/00326* (2013.01)

(56) References Cited

U.S. PATENT DOCUMENTS

| | | |
|---|---|---|
| 4,435,173 A | 3/1984 | Siposs et al. |
| 4,547,189 A | 10/1985 | Moore, Jr. |
| 4,846,797 A | 7/1989 | Howson et al. |
| 5,097,122 A | 3/1992 | Colman et al. |
| 5,505,709 A | 4/1996 | Funderbuck et al. |
| 2003/0111494 A1 | 6/2003 | Ling |
| 2003/0195491 A1 | 10/2003 | Schneider et al. |
| 2004/0064096 A1 | 4/2004 | Flaherty |
| 2004/0159675 A1 | 8/2004 | Nishino |
| 2007/0264725 A1 | 11/2007 | Wiggli |
| 2008/0077081 A1 | 3/2008 | Mounce et al. |
| 2008/0156117 A1 | 7/2008 | Londo |
| 2009/0047440 A1 | 2/2009 | Giri et al. |
| 2009/0104078 A1 | 4/2009 | Seguin |
| 2009/0143735 A1 | 6/2009 | De Polo |
| 2009/0158862 A1 | 6/2009 | Londo |

FOREIGN PATENT DOCUMENTS

| | | |
|---|---|---|
| JP | 9101315 | 4/1997 |
| WO | 2004/009238 | 1/2004 |
| WO | 2005/094921 | 10/2005 |
| WO | 2006/089103 | 8/2006 |

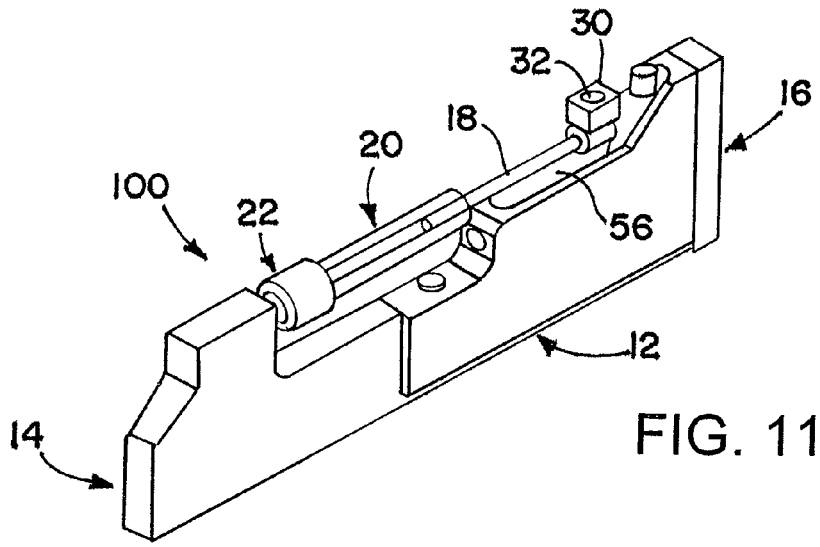
FIG. 11
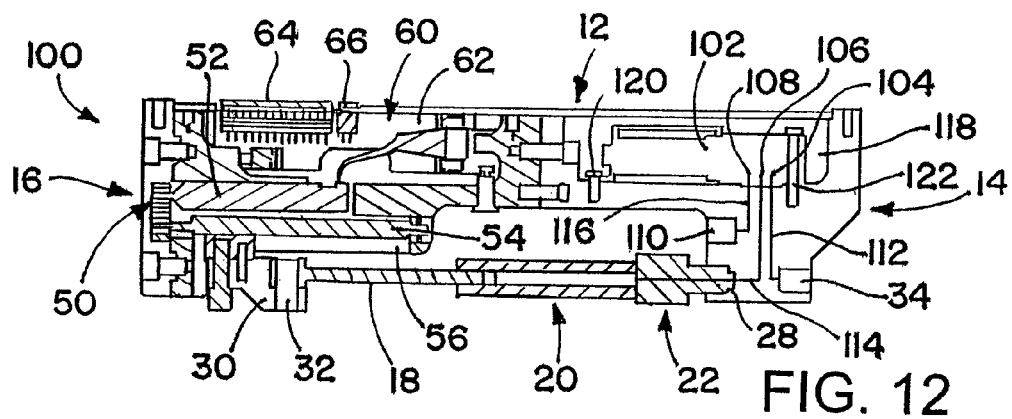
FIG. 12
FIG. 13

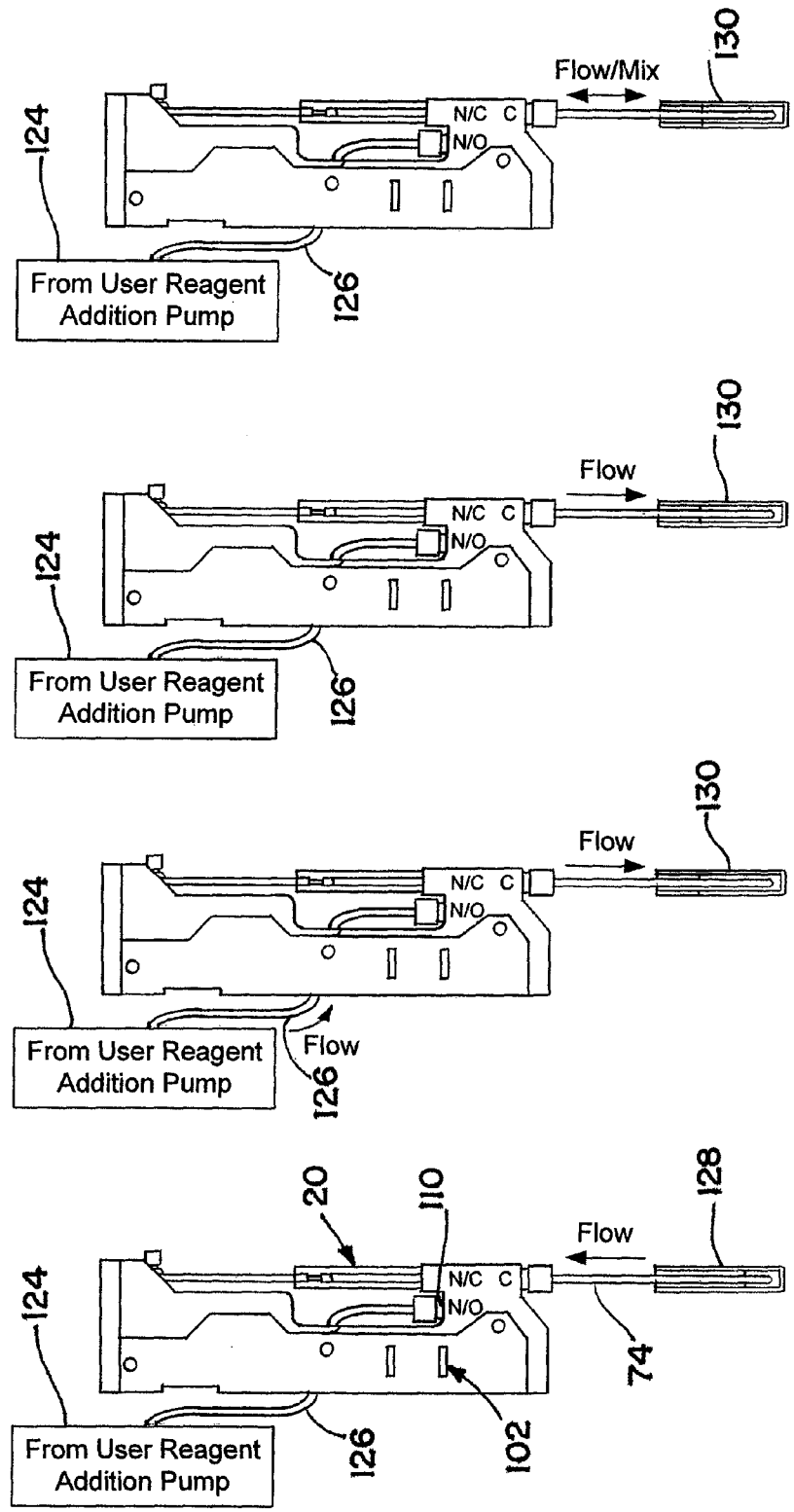

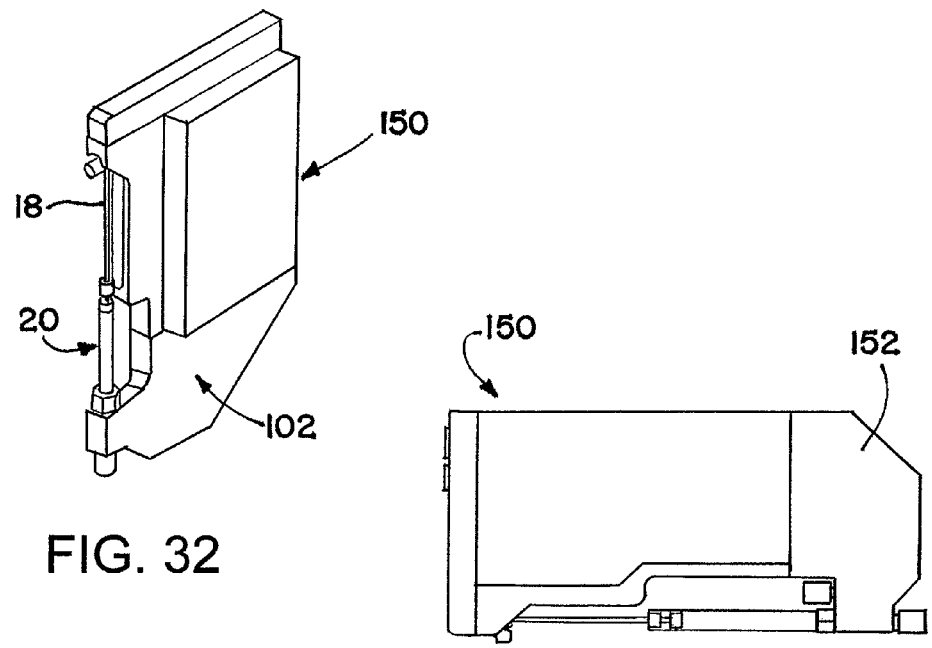
FIG. 32
FIG. 33
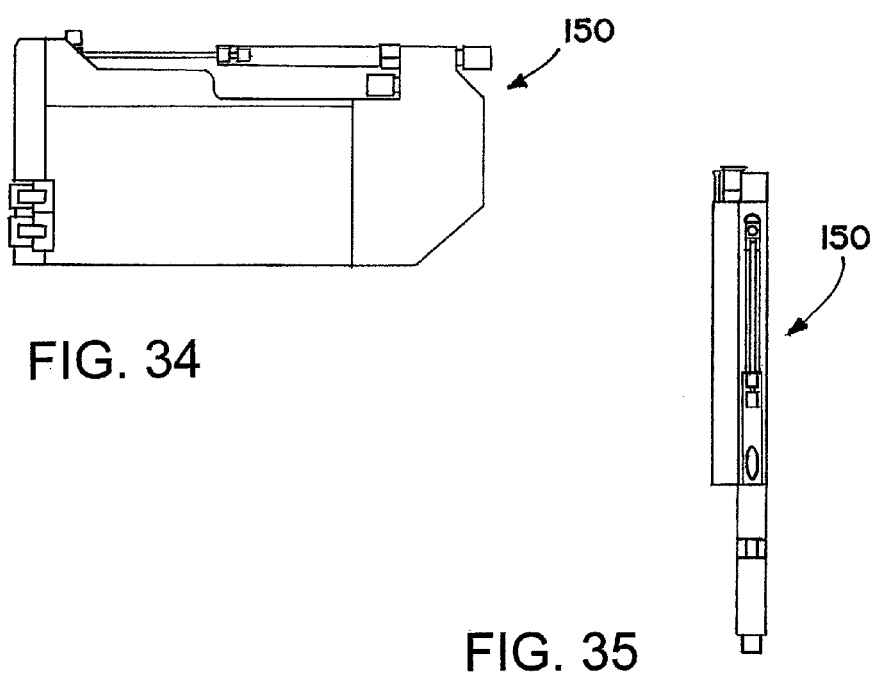
FIG. 34
FIG. 35

MINIATURIZED SYRINGE PUMP SYSTEM AND MODULES

RELATED APPLICATION

This application is a national phase of International Application No. PCT/US2011/039264 filed Jun. 6, 2011 and published in the English language, which claims the benefit of U.S. Provisional Application No. 61/351,550 filed Jun. 4, 2010.

FIELD OF THE INVENTION

The invention herein described relates generally liquid handling devices and systems having particular application in laboratory sample management systems for analytical applications, and more particularly to a miniaturized syringe pump and pump system useful for manipulation and transfer of reagents and samples in conjunction with micro-titration plates having spaced sample wells in a grid.

BACKGROUND

Liquid handling devices heretofore have been used to provide for aspirating and/or dispensing an agent. These devices include syringe pumps that are typically located remotely from the sample wells due to typical syringe pump form factor. This presents various challenges for basic liquid handing. Remote pumps require long tube lengths, which extend through robotic system cable/fluidic management systems. This causes fundamental fluid handling issues regarding liquid dispense precision, accuracy and long term reliability.

SUMMARY OF THE INVENTION

The present invention provides various improvements in liquid handling devices and particularly syringe pumps that no longer need to be located remotely from the sample wells.

According to one aspect of the invention, a liquid handling device, in particular a syringe pump, is provided for use in a liquid handling system and includes a plurality of the liquid handling devices assembled in side-by-side relationship at a center-to-center spacing of X. The device includes a barrel, a plunger movable in the barrel for dispensing or aspirating liquid from or into the barrel, an electrically powered motive device for moving the plunger in the barrel for dispensing or aspirating liquid from or into the barrel, and electronics for controlling the motor and for communicating with an external component. The barrel, plunger, motive device and electronics are assembled together in an envelope having a front portion including at least the barrel and plunger, and a rear portion including at least a portion of the electronics. The rear portion has a thickness greater than X but no greater than 2X, and the front portion has a thickness no greater than X and is laterally offset relative to a center plane of the envelope, whereby the liquid handling device can be assembled with another reversely oriented liquid handling device at a center-to-center spacing of X and a total combined width no greater than 2X.

The liquid handling device can include a valve contained within the envelope, wherein the electronics control operation of the valve. The valve may include a first port connected to a dispensing/aspirating lumen, in particular a syringe needle, a second port connected to the barrel, and a third port connected to an inlet that provides for connection of the liquid handling device to a source of or reservoir for a liquid.

According to another aspect of the invention, a liquid handling device is provided for use in a liquid handling system including a plurality of the liquid handling devices assembled in side-by-side relationship at a center-to-center spacing of X. The device includes a barrel, a dispensing/aspirating lumen, a plunger movable in the barrel for dispensing or aspirating liquid from or into the barrel, an electrically powered motive device for moving the plunger in the barrel for dispensing or aspirating liquid from or into the barrel, a valve having a first port connected to the dispensing/aspirating lumen, in particular a syringe needle, a second port connected to the barrel, and a third port connected to an inlet that provides for connection of the liquid handling device to a source of or reservoir for a liquid, and electronics for controlling the motor and valve.

The plunger, motive device, valve and electronics are assembled together in an envelope having a thickness no greater than X.

The liquid handling device may also include a plurality of liquid handling devices assembled at a center-to-center spacing of X.

According to still another aspect of the invention, a liquid handling device is provided for use in a liquid handling system that includes a housing having spaced apart first and second end portions defining therebetween an opening for receiving a barrel and a plunger reciprocally movable in the barrel. The barrel is removably attachable to the first end portion and the plunger is pivotally attachable to a linearly movable carriage, whereby upon separation of the barrel from the first end, the barrel is rotated out of a plane of the liquid handling device for placement of a different barrel.

The liquid handling device may include a valve having a first port connected to a dispensing/aspirating lumen, in particular a syringe needle, a second port connected to the barrel, and a third port connected to an inlet that provides for connection of the liquid handling device to a source of or reservoir for a liquid. Alternatively, the first port may be connected to the barrel and the second port is connected to the dispensing/aspirating lumen, in particular the syringe needle.

The liquid handling device may have a thickness no greater than X. The liquid handling device may also include a plurality of liquid handling devices assembled at a center-to-center spacing of X.

According to yet another aspect of the invention, a liquid handling device for use in a liquid handling system includes a housing having spaced apart first and second end portions defining therebetween an opening for receiving a barrel, a dispensing/aspirating lumen, a plunger movable in the barrel for dispensing or aspirating liquid from or into the barrel, and an electrically powered motive device for moving the plunger in the barrel for dispensing or aspirating liquid from or into the barrel, and an electronics module removably mounted to the housing.

Further features of the invention will become apparent from the following detailed description when considered in conjunction with the drawings.

BRIEF DESCRIPTION OF THE DRAWINGS

FIG. 11 is a perspective view of another exemplary liquid handling device in accordance with the invention;

FIG. 12 is a side cross-sectional view of the liquid handling device of FIG. 11;

FIG. 13 is a side view of the liquid handling device of FIG. 11;

FIG. 17 is a side view of the liquid handling device of FIG. 14 coupled to a user reagent addition pump;

FIG. 18 is another side view of the liquid handling device of FIG. 14 coupled to the user reagent addition pump;

FIG. 19 is yet another side view of the liquid handling device of FIG. 14 coupled to the user reagent addition pump;

FIG. 20 is still another side view of the liquid handling device of FIG. 14 coupled to the user reagent addition pump;

FIG. 32 is a perspective view of a further exemplary liquid handling device in accordance with the invention;

FIG. 33 is a right side view of the liquid handling device of FIG. 32;

FIG. 34 is a left side view of the liquid handling device of FIG. 32;

FIG. 35 is a front view of the liquid handling device of FIG. 32;

DETAILED DESCRIPTION

Figure 1:
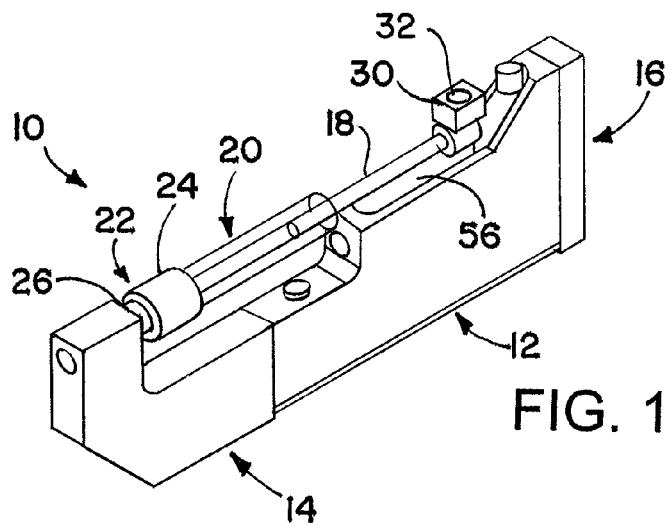
FIG. 1 is a perspective view an exemplary liquid handling device in accordance with the invention.
Figure 2:
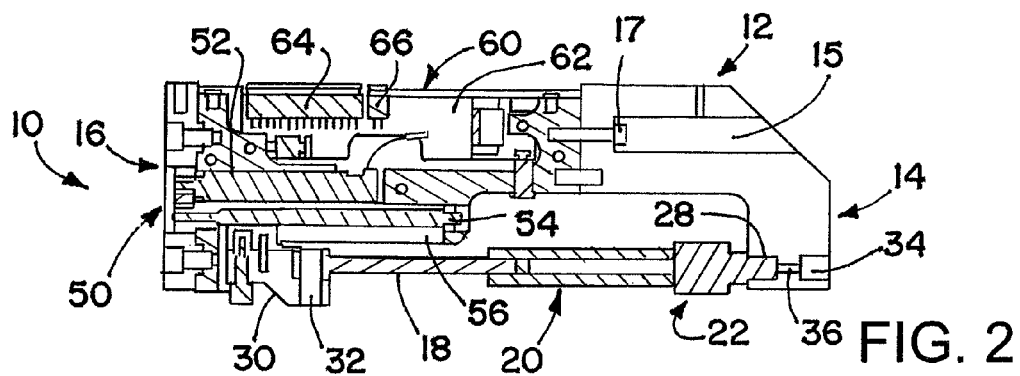
FIG. 2 is a side cross-sectional view of the liquid handling device of FIG. 1.

Because the invention was conceived and developed for use in handling liquids in analytical processes and especially bioanalytical processes such as introducing samples into LC systems, HPLC systems, etc., it will be herein described chiefly in this context. More particularly, the invention will be described in the context of a small form factor syringe pump system that can be configured as a plurality of devices intended to be utilized for aliquot operations in an automated liquid handling instrument. Typical containers for samples are micro-titration plates which typically have arrangements of wells on 9 mm centers (e.g. 96 well plates) and 4.5 mm centers (e.g. 384 well plates). The syringe pump system can be adapted to variable distance spanning motion technologies, which enables a plurality of tips to be distanced at centers greater than 9 mm for use with larger format sample collection media, e.g. vacutainers, sample vials or other larger diameter collection tubes. More generally, the principles of the invention in their broader aspects can be adapted to other types of systems.

Referring now in detail to the drawings and initially to FIGS. 1-4, an exemplary embodiment of a liquid handling device 10 is shown. The liquid handling device generally comprises a housing 12 having opposite end portions 14 and 16, herein referred to as first end portion 14 and second end portion 16, forming a window where a plunger 18 and a barrel 20 are disposed. The first end portion 14 includes a recess 15 that opens to a rear of the second end portion 16, the recess providing an access to at least one fastener 17 that secures the first end portion to the second end portion.

The barrel 20 is provided with an end connector 22 having a knurled surface 24 for hand screwing and a threaded portion 26 configured to be received in a threaded bore 28 in the housing 12. The barrel receives the plunger 18 at an opposite end from the connector 22, and the plunger 18 is pivotally connected to a carriage 30 by a pin 32. The carriage 30 is configured to drive the plunger 18 in a bore of the barrel 20 for aspirating/dispensing fluid in/out of the barrel and from/to a fluid component (FIG. 7, numeral 74), such as a syringe needle. The syringe needle 74 is connected to a port 34 in the first end portion 14 and receives/delivers fluid from/to the barrel 20 via a passage 36 in the first end portion 14.

Figure 5:
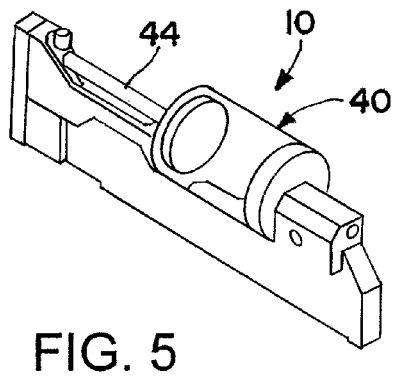
FIG. 5 is a perspective view of the liquid handling device of FIG. 1 including a replacement barrel.
Figure 6:
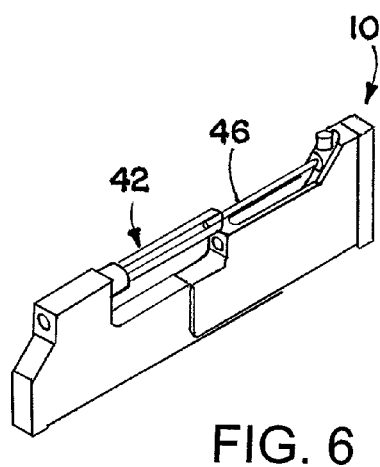
FIG. 6 is a perspective view of the liquid handling device of FIG. 1 including a replacement having a barrel with a diameter smaller than the barrel of FIG. 5.

As will be appreciated, the barrel 20 may be easily replaced by a barrel having the same or different diameter with a different volume, as shown in FIGS. 5 and 6. The barrels may have, for example, a 5 miroliter to a 5 milliliter liquid volume and a 30 mm stroke length. The barrel 20 can be replaced by unscrewing the end connector 22 from the threaded bore 28, and once the end connector is clear of the first end portion 14, the barrel can be pivoted out of a plane of the housing 12. Then the barrel 20 can be removed and another barrel, such as barrel 40 or 42 can be coupled to the plunger 18 and secured to the housing 12 as described above. Alternatively, the plunger 18 and the barrel 20 may both be removed and replaced by another plunger and barrel having the same or different diameters, such as by plunger 44 and barrel 40 or by plunger 46 and barrel 42, and the replacement plunger and barrel may be coupled to carriage 30 and secured to the housing 12 as described above.

Referring again to FIGS. 1-4, the liquid handling device 10 includes in the second end portion 16 a drive mechanism 50 including a motive device, such as an electric rotary motor 52 connected by gears to a rotary-to-linear motion transfer device including a rotating drive screw 54 in mesh with the carriage 30, preferably by means of a nut forming part of the carriage. The rotating drive screw 54 extends parallel to the movement direction of the plunger 18 and effects rotation of the plunger 18. The drive screw 54 may be coplanar with the motor 52 and may be laterally offset and at least partially coextensive with the plunger 18. The carriage 30 is constrained from rotation by a guide slot 56 in the housing 12 and the carriage 30 linearly drives the plunger 18.

The liquid handling device 10 also includes in the second end portion 16 onboard electronics 60 for controlling the motor 52 and for communicating with an external component. The electronics may include a printed circuit board 62 and external connectors 64 and 66 preferably at a backside of the housing 12. The connectors are provided to connect with an external component for receiving instructions for controlling the device, such as dispersing a certain amount of fluid, aspirating a certain amount of fluid, etc. The electronics may be onboard as shown, may be off-board as described below, or be both onboard and off-board. Moreover, the liquid handling device 10 may have wireless communications and therefore also include an onboard power source (not shown). Additionally or alternatively, the device 10 may be tethered to an off-board power source in any suitable manner.

Figure 3:
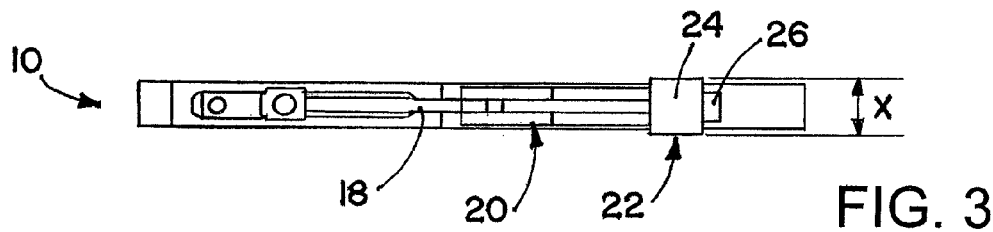
FIG. 3 is a front view of the liquid handling device of FIG. 1.
Figure 4:
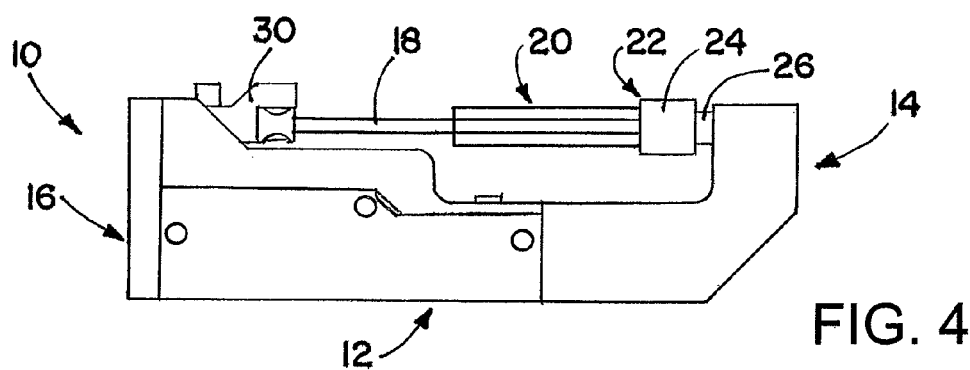
FIG. 4 is a side view of the liquid handling device of FIG. 1.

As shown in FIG. 3, the liquid handling device 10 has a thickness X. The thickness X correlates to the spacing between wells of a titration plate which the liquid handling device is intended to be used with. Conventional wells are on 9 mm and 4.5 mm centers, hence the thickness X may be no greater than 9 mm in one embodiment and 4.5 mm in another embodiment. This is shown for example in FIG. 7, where a plurality of liquid handling devices are shown in side by side relation to one another, forming a bank of liquid handling devices. The bank of liquid handling devices is assembled at a center-to-center spacing of X.

Figure 7:
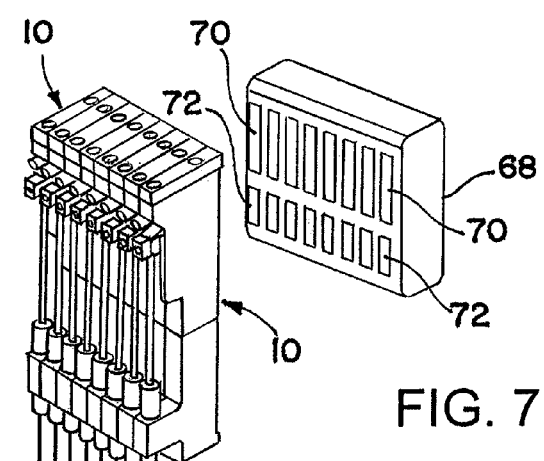
FIG. 7 is a perspective view of a bank of liquid handling devices coupled together and configured to mate with an electronic control module.

Turning now in detail to the alternate embodiment shown in FIG. 7, the plurality of liquid handling devices 10 have an electronic control module 68 removably mounted to the housings of the bank of devices 10. The electronic control module 68 has a plurality of plug-together mating connectors 70, 72 that mate with respective plug-together mating connectors 64, 66 on the devices 10 for electrically connecting the electronic control module 68 to electrical circuitry in the respective housings 12. The module 68 may be disposed in rear portions of the housings 12.

It will be appreciated that when the electronic control module 68 is coupled to the devices 10, the devices and control module still have a thickness less than or equal to nX, n being the number of devices 10 in the bank. The electronic control module 68 may be used in conjunction with or in place of the onboard electronics 60, and may provide motor control, communications and power to the devices 10. The control module may also include a power reduction circuit to reduce heat generation.

Figure 8:
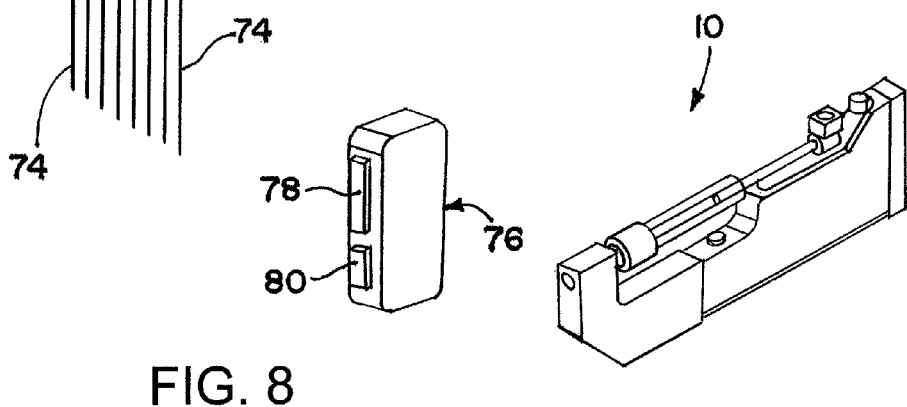
FIG. 8 is a perspective view of the liquid handling device configured to mate with an electronic control module.

In another alternate embodiment shown in FIG. 8, each device 10 may have a respective electronic control module 76 removably mounted to the housing 12. The electronic control module 76 and the housing 12 have respective plug-together mating connectors 78, 80 and 64, 66 for electrically connecting the electronic control module to electrical circuitry in the housing. The module 76 may be disposed in a rear portion of the housing 12.

The module 76 forms in essence part of the housing 12 but still is removable. It will be appreciated that when the electronic control module 76 is coupled to the device 10, the device and control module still have a thickness less than or equal to x. The electronic control module 76 may be used in conjunction with or in place of the onboard electronics 60, and may provide motor control, communications and power to the device 10.

Figure 9:
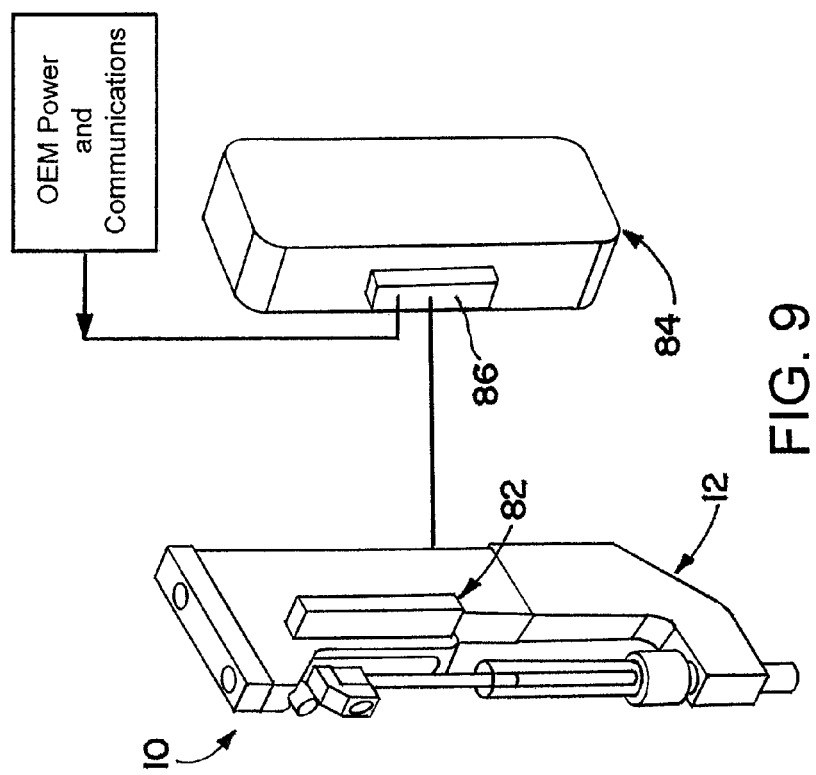
FIG. 9 is a perspective view of the liquid handling device configured to mate with a communication module.

In still another alternate embodiment shown in FIG. 9, each device 10 may have a respective onboard miniaturized electronic motor control 82 with a communications input. The motor control 82 is configured to mate with a communication module 84 via a connector 86. The communication module 84 is a communication converter module to allow use of various standardized communications protocols, which may be wired or wireless protocols. The communication wires to each device 10 may be daisy chained to reduce wire count.

Figure 10:
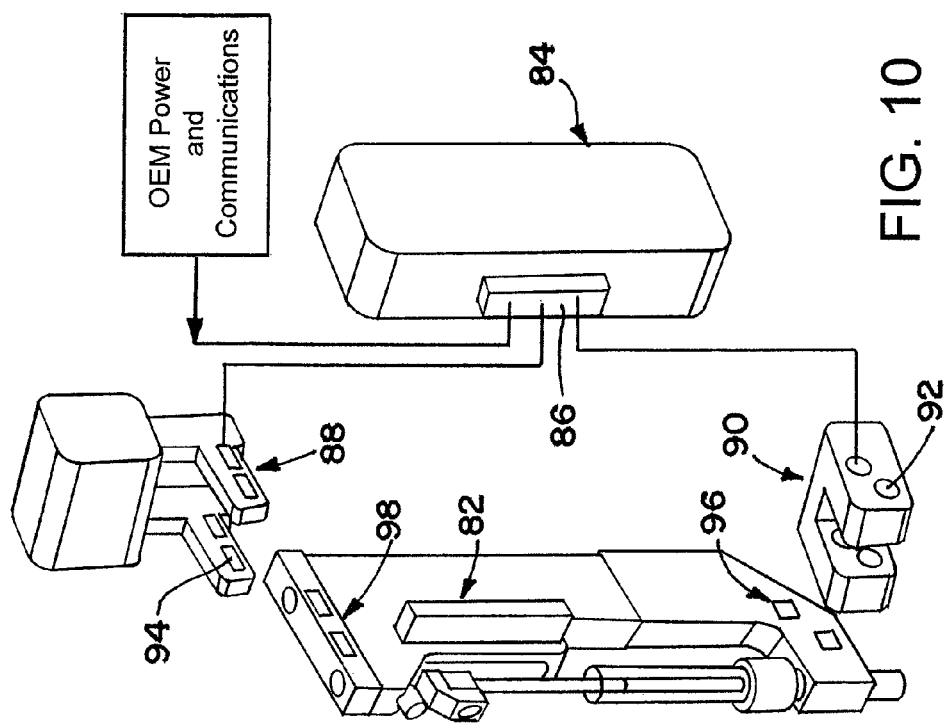
FIG. 10 is a perspective view of the liquid handling device configured to mate with the communication module and communicate with a gripper and/or a docking station.

In a further embodiment shown in FIG. 10, each device 10 may mate with the communication module 84 as described above, and may also have the capability to operate aspirate or dispense sequences while in a mobile gripper 88 and/or in a docking station 90. The gripper 88 and docking station 90 have contacts 92 and 94 that mate with contacts 96 and 98 on the outside of the housing 12. The contacts 92 and 94 are electrically isolated and provide power and communication signals to the device 10 via the contacts 96 and 98. In this way, the device 10 may have pick-up and drop-off features incorporated therein.

Turning now to FIGS. 11-13, another exemplary embodiment of a liquid handling device is shown as reference numeral 100. This device 100 is the same as the device 10 shown in FIGS. 1-4 except as noted below, and accordingly, the same reference numerals are being used to describe like components. In this embodiment, the liquid handling device 100 is configured to function as a syringe pump, and accordingly includes a valve 102, such as a solenoid valve, disposed in the first end portion 14. The device 100 may include electronics 60 (or additional electronics) that can allow for pulse-width-modulated valve control for heat reduction and power conservation.

The valve 102 has a first port 104 connected to the syringe needle 74 via port 34, a second port 106 connected to the barrel 20, and a third port 108 connected to an inlet 110 that provides for connection of the liquid handling device 100 to a source of or reservoir for a liquid. The device 100 includes flow passages 112, 114 and 116 that are connected to the ports 104, 106 and 108 and the port 34, barrel 20 and inlet 110, respectively. As shown in FIG. 13, the bore 28 to which the barrel is coupled is the common port C of the liquid handling device 100, the port 34 is the normally closed port N/C and the inlet 110 is the normally open port N/O.

The valve 102 may be coplanar with the motor 52 and electronics 60 and may be longitudinally displaced from the motor and electronics. Accordingly, as discussed above, the valve 102, together with the plunger 18, motor 52 and electronics 60 are assembled together in an imaginary envelope having a thickness no greater than X.

The liquid handling device 100 may also include a cutout 118 for the valve 102 in the first end portion 14. The cutout provides an access to the at least one fastener 17 that secures the first end portion 14 to the second end portion 16. After the first end portion has been secured to the second end portion, the valve 102 can be installed in the cutout and secured by suitable fasteners, such as fasteners 120 and 122. The cutout 118 may then be closed on a side by a plate and on a back wall by a back plate, which may be secured in any suitable manner. Alternatively, the cutout 118 may be closed on the side and the back wall by a single plate.

Figure 14:
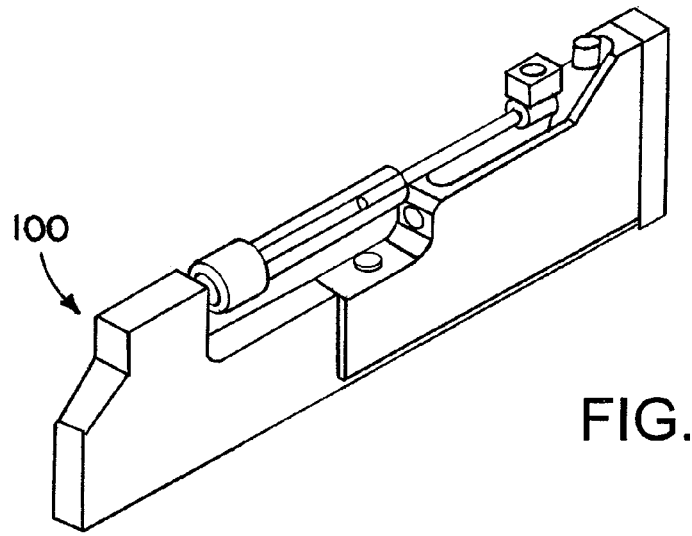
FIG. 14 is a perspective view of yet another exemplary liquid handling device in accordance with the invention.
Figure 15:
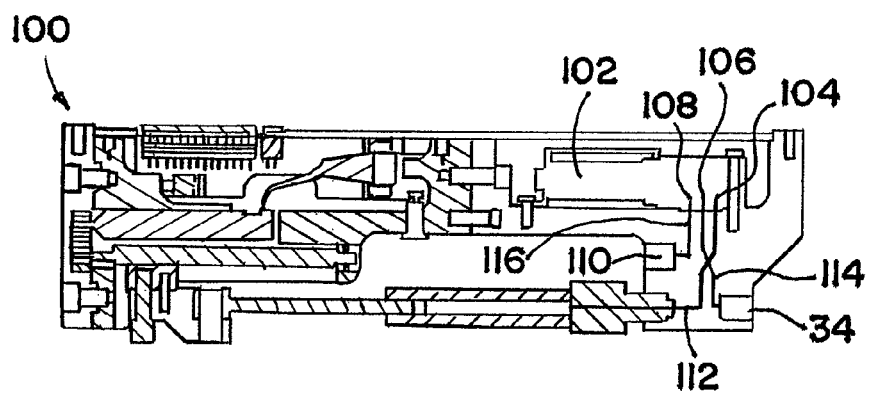
FIG. 15 is a side cross-sectional view of the liquid handling device of FIG. 14.
Figure 16:
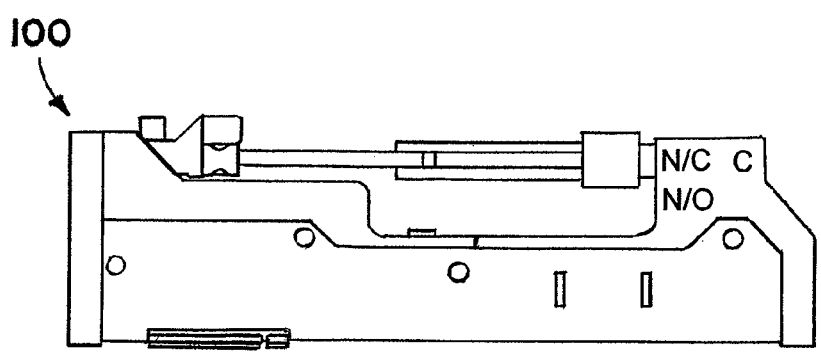
FIG. 16 is a side view of the liquid handling device of FIG. 14.

Turning now to FIGS. 14-20, another embodiment of the liquid handling device 100 is shown wherein the passages 112 and 114 are crossed. Accordingly, the first port 104 is connected to the barrel 20 and the second port 106 is connected to the syringe needle 74 via port 34. This configuration is provided to allow for user reagent addition. As shown in FIG. 16, the bore 28 to which the barrel is coupled is the normally closed port N/C, the port 34 is the common port C and the inlet 110 remains the normally open port N/O.

As shown in FIGS. 17-20, a user reagent addition pump 124 is provided that is coupled by a supply line 126 to the inlet 110. The supply line may run through a bore in the housing 12 or may run along an outside of the housing. As shown in FIG. 17, the syringe 74 is filled with a sample from a sample container 128 and the sample is held in the barrel 20. Then, as shown in FIG. 18, reagents or diluents from the pump 124 are added into a different sample container 130. Next, as shown in FIG. 19, the sample is delivered from the barrel 20 through the syringe 74 and added to the reagents or diluents in sample container 130. Then, as shown in FIG. 20, the sample and reagents or diluents may optionally be mixed, for example by drawing the sample and reagents or diluents into the barrel 20 and then returning the mixture to the sample container 130. The mixing step may be repeated if desired.

Figure 21:
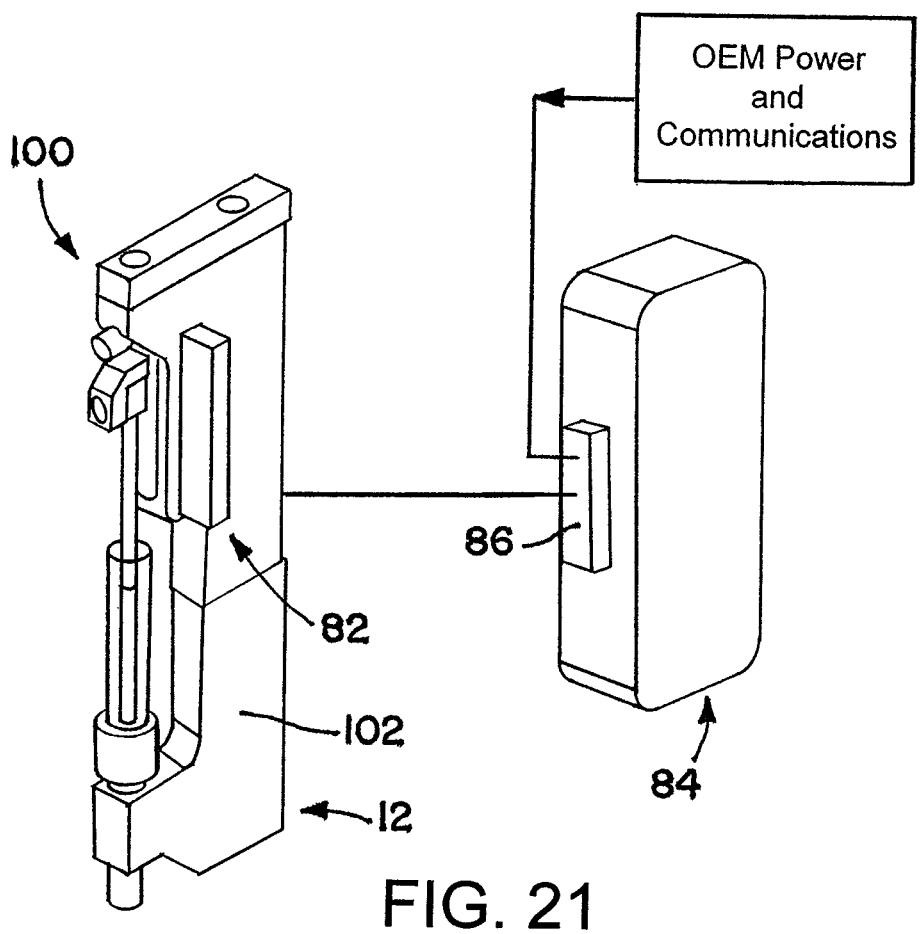
FIG. 21 is a perspective view of the liquid handling device of FIG. 11 or 14 configured to mate with a communication module.

Turning now to FIG. 21, another embodiment is shown wherein the liquid handling device 100 is mated with the communication module 84 as discussed above in FIG. 9.

Figure 22:
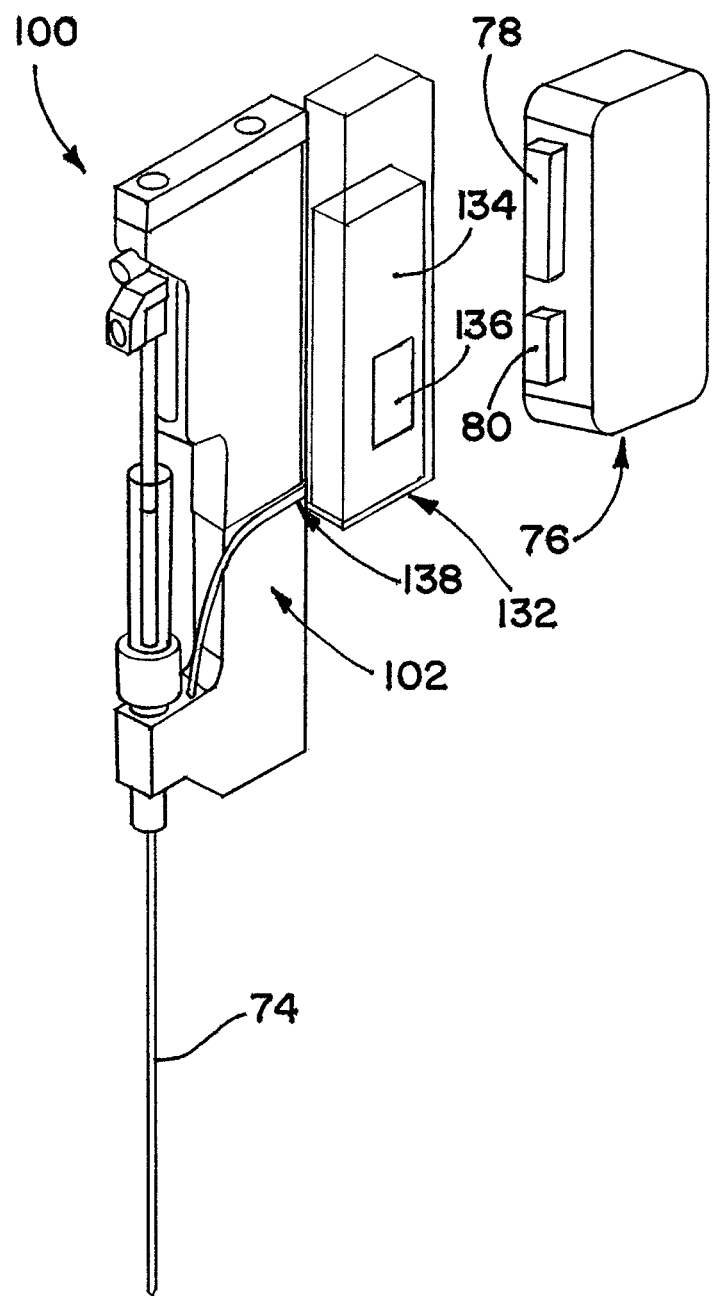
FIG. 22 is a perspective view of the liquid handling device of FIG. 11 or 14 configured to mate with a control module and communicate with a reservoir.

Turning now to FIG. 22, still another embodiment is shown wherein the liquid handling device 100 is mated with the electronic control module 76 as discussed above in FIG. 8. In this embodiment, however, the liquid handling device 100 also includes a detachable reservoir 132. The inclusion of the reservoir can reduce fluidic complexity verses traditional liquid handling systems and can increase sample handling throughput. The reservoir may include a sample cartridge 134 that can have various volumes of various liquids. The cartridge 134 may be removable, reusable or disposable, and may be traceable, for example by barcode 136. The cartridge 134 may be coupled to the inlet 110 via a supply line 138.

Figure 23:
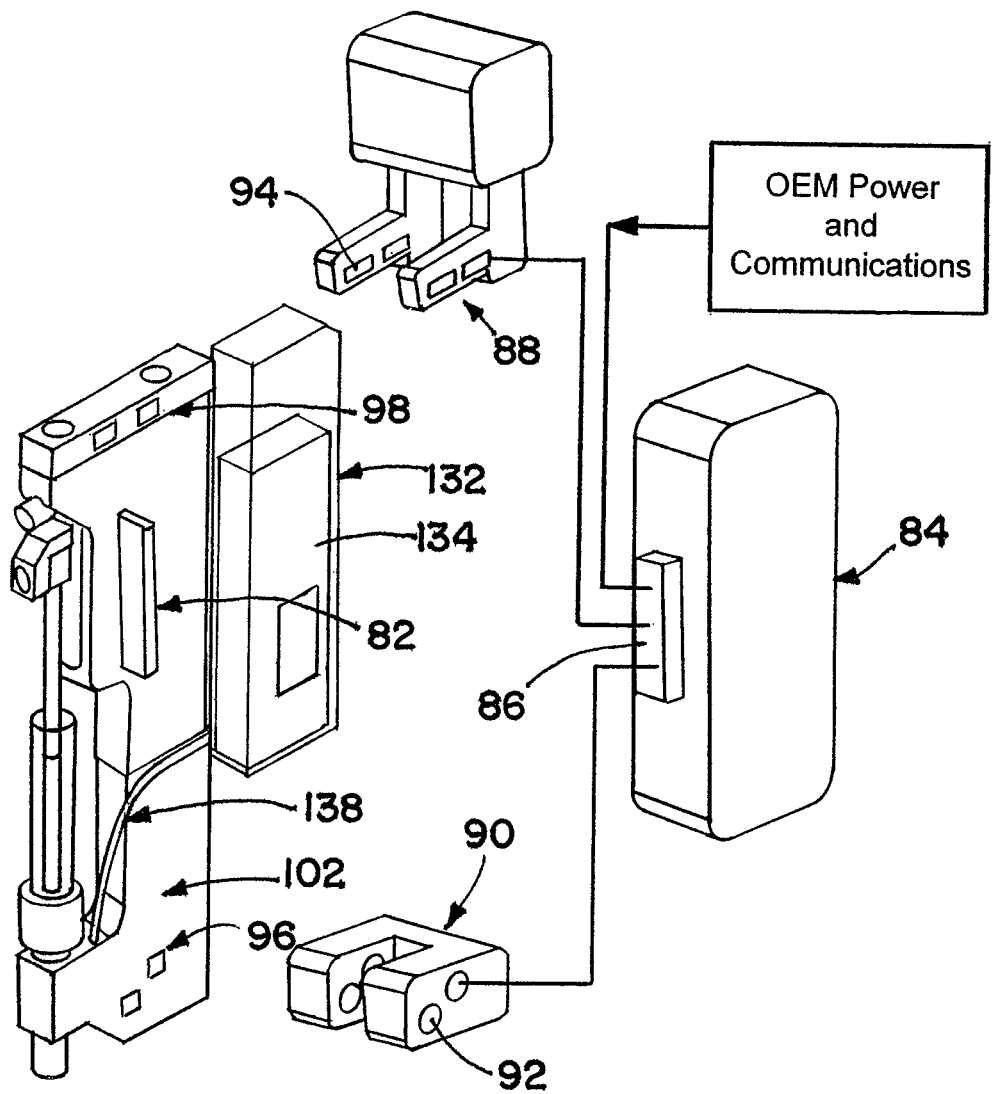
FIG. 23 is a perspective view of the liquid handling device of FIG. 22 configured to communicate with a gripper and/or a docking station.
Figure 24:
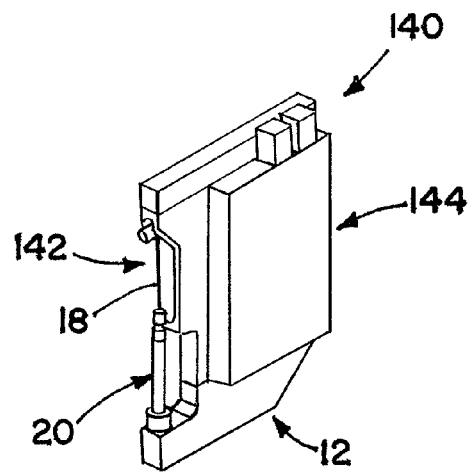
FIG. 24 is a perspective view of yet another exemplary liquid handling device in accordance with the invention.
Figure 25:
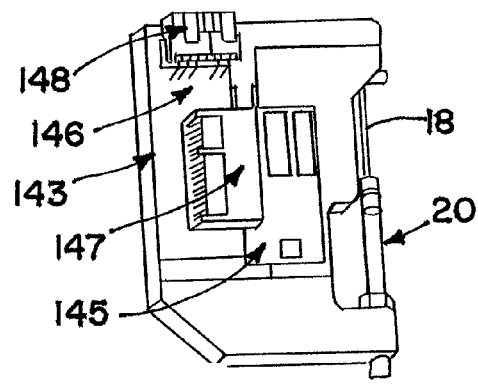
FIG. 25 is a perspective view of the liquid handling device of FIG. 24 with a cover removed.

Turning now to FIG. 23, a further embodiment is shown that is similar to FIG. 22, but which may also have the capability to operate aspirate or dispense sequences while in a mobile gripper 88 and/or in a docking station 90, as described above in FIG. 10.

Turning now to FIGS. 24-31, another exemplary embodiment of a liquid handling device is shown as reference numeral 140. This device 140 is similar to the device 10 shown in FIGS. 1-4 except as noted below, and accordingly, the same reference numerals are being used to describe like components.

The device 140 includes a barrel, plunger and drive assembly, which can be the same as that shown in FIGS. 1-4, assembled together in an envelope having a front portion 142 including at least the barrel and plunger. The plunger 18 may be coupled to the carriage 30 as described above or may be coupled to the front portion in any other suitable manner.

The envelope includes a rear portion 144 including at least a portion of electronics 143, which may be unitary with the housing 12. As shown, the electronics 143 can include a motor control board 145 and an adaptor board 146 to provide motor control and communications. The motor control board 145 includes a connector 147 coupled to the adaptor board, such as by soldering pins of the connector to the board 146. The electronics also include a connector 148, which can provide a 6-wire connection to a remote controller or network for receiving communications to and/or from the device and for providing power to the device. Alternatively, the electronics may be similar to the electronics discussed above in FIG. 1 or included in an electronic control module removably mounted to the housing 12 and contained within the envelope, as discussed above regarding FIG. 8.

Figure 26:
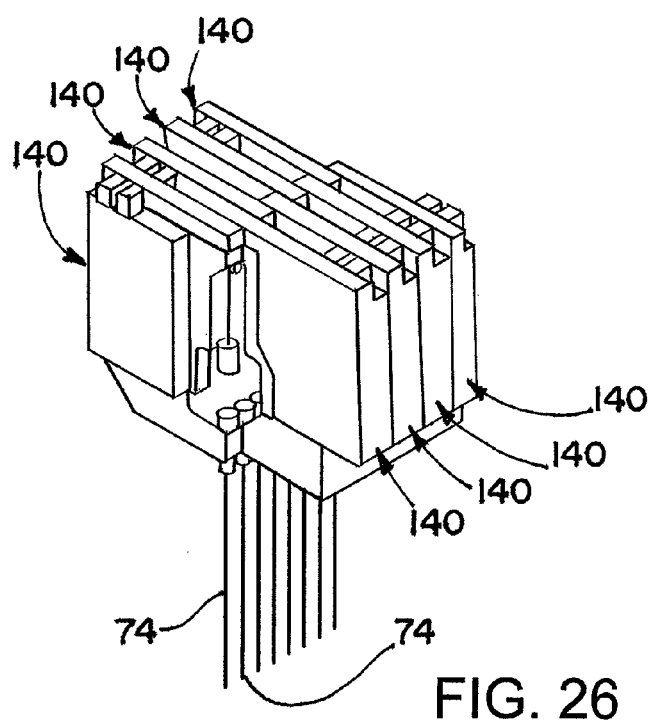
FIG. 26 is perspective view of a bank of the liquid handling devices of FIG. 24.
Figure 27:
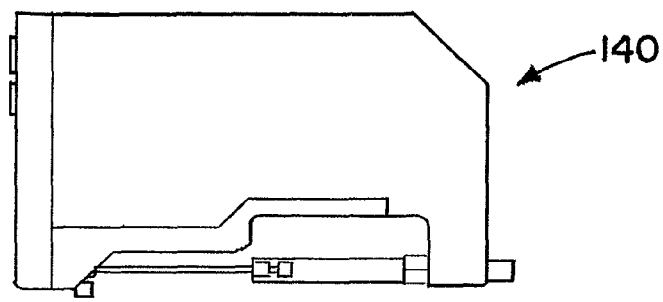
FIG. 27 is a right side view of the liquid handling device of FIG. 24.
Figure 28:
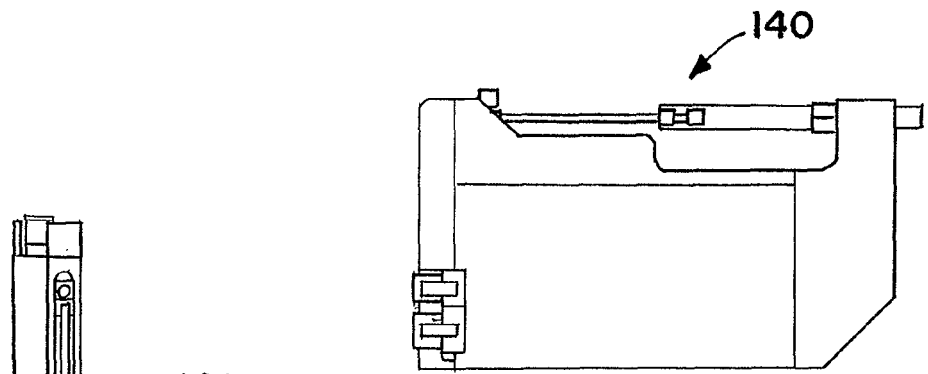
FIG. 28 is a left side view of the liquid handling device of FIG. 24.
Figure 29:
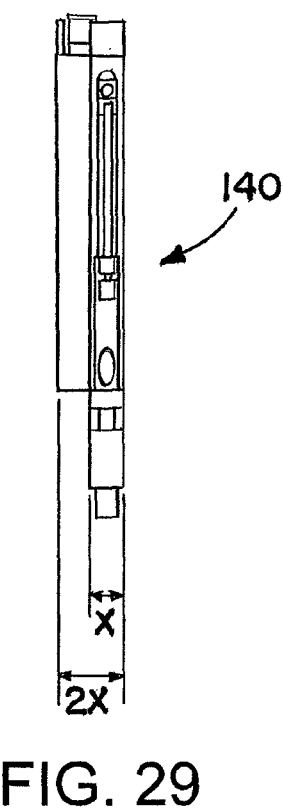
FIG. 29 is a front view of the liquid handling device of FIG. 24.
Figure 30:
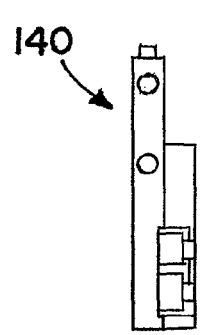
FIG. 30 is a top view of the liquid handling device of FIG. 24
Figure 31:
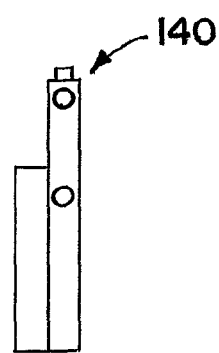
FIG. 31 is a bottom view of the liquid handling device of FIG. 24.

The rear portion 144 has a thickness greater than X but no greater than 2X, and the front portion has a thickness no greater than X and is laterally offset relative to a center plane of the envelope. The liquid handling device 140 can be assembled with another reversely oriented liquid handling device at a center-to-center spacing of X and a total combined width no greater than 2X. In this way, any suitable electronics having a thickness no greater than 2X may be used, such as commercially available electronics. For example, as shown in FIG. 26, eight reversely oriented liquid handling devices 140 are provided. If the devices are to be wired, all wires associated with communication can be daisy chained to reduce the wire count.

Turning now to FIGS. 32-35, another exemplary embodiment of a liquid handling device is shown as reference numeral 150. This device 150 is the same as the device 130 shown in FIGS. 24-31 except the device 150 includes a valve 102, a portion of which is shown through plate 152 suitably coupled to the housing 12. The device 150 is also longer than the device 130 to provide space for the valve without increasing the thickness of the device 150. The valve may be oriented as shown in FIGS. 11-13 or as shown in FIGS. 14-16.

Figure 36:
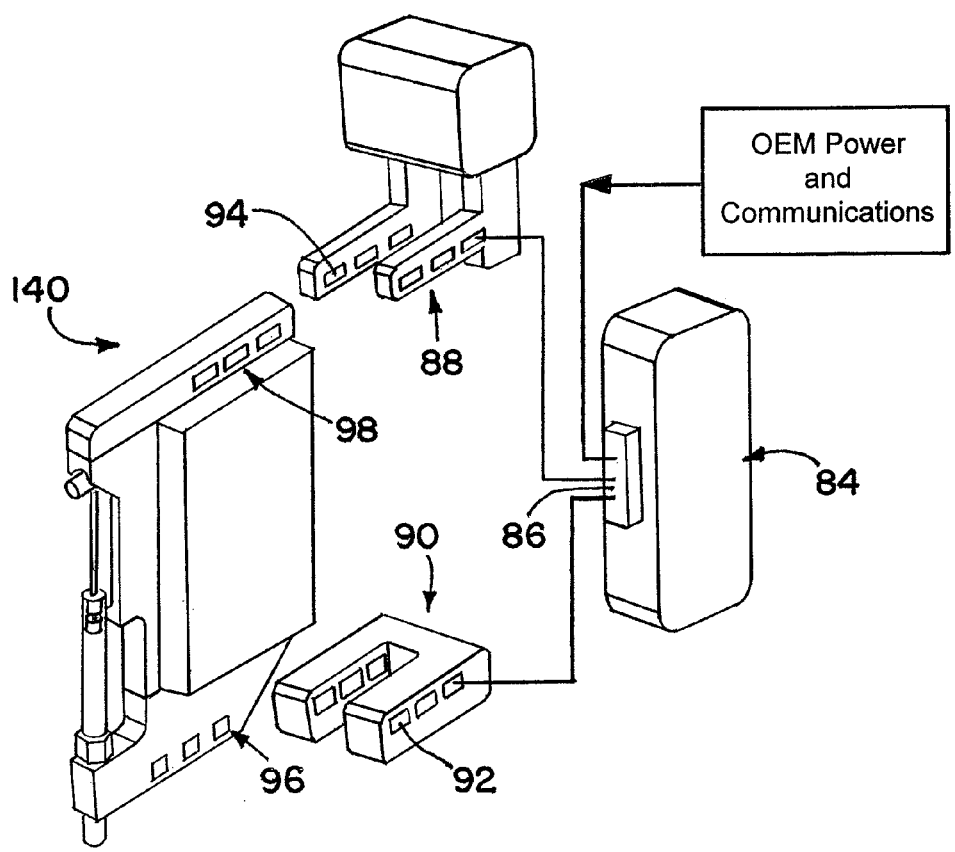
FIG. 36 is a perspective view of the liquid handling device of FIG. 24 configured to mate with the communication module and communicate with a gripper and/or a docking station.

Turning now to FIG. 36, another embodiment of the liquid handling device 140 is shown. The liquid handling device may mate with the communication module 84 as described above in FIG. 9, and may operate while in a mobile gripper 88 and/or in a docking station 90 as described above in FIG. 10.

Figure 37:
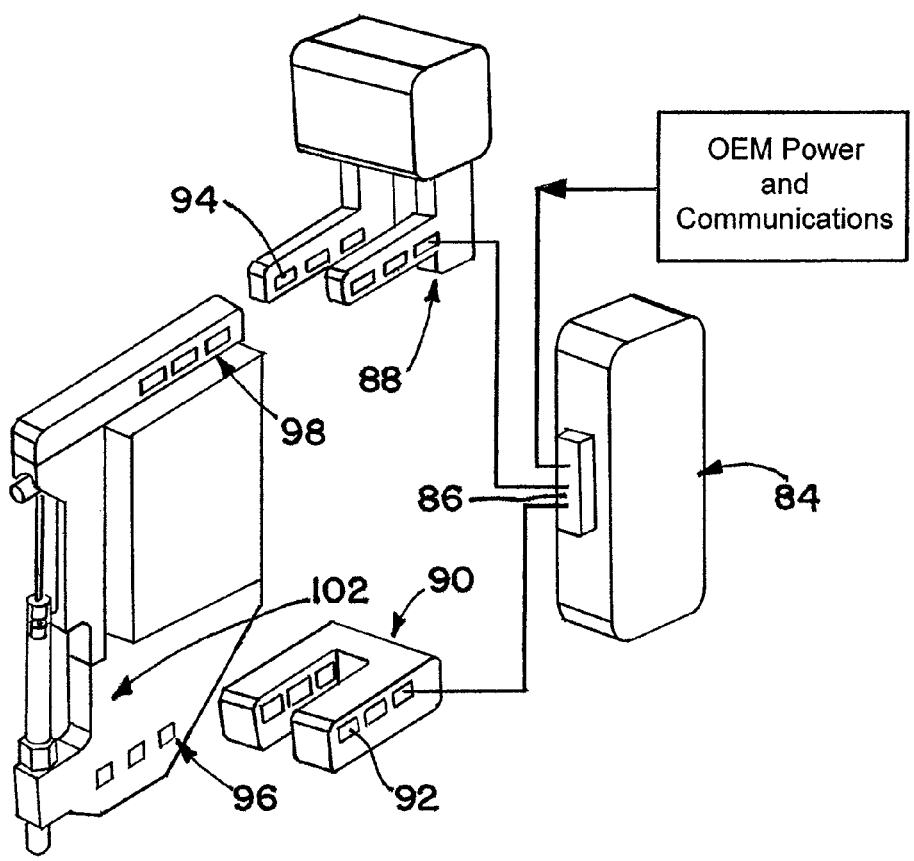
FIG. 37 is a perspective view of the liquid handling device of FIG. 32 configured to mate with the communication module and communicate with a gripper and/or a docking station.

Turning now to FIG. 37, another embodiment of the liquid handing device 150 is shown. The liquid handling device may mate with the communication module 84 as described above in FIG. 9, and may operate while in a mobile gripper 88 and/or in a docking station 90 as described above in FIG. 10.

The above described liquid handling devices may be coupled to a suitably programmed computer and/or computer network for executing command signals for carrying out the required operations.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A liquid handling device, in particular a syringe pump, for use in a liquid handling system including a plurality of the liquid handling devices assembled in side-by-side relationship at a center-to-center spacing of X, the device including:
   a barrel,
   a plunger movable parallel to a longitudinal axis in the barrel for dispensing or aspirating liquid from or into the barrel,
   an electrically powered motive device for moving the plunger in the barrel for dispensing or aspirating liquid from or into the barrel, and
   electronics for controlling the motive device and for communicating with an external component,
   wherein the barrel, plunger, motive device and electronics are assembled together in an envelope having a front portion including at least the barrel and plunger, and a rear portion that is offset along a lateral axis from the front portion and that includes at least a portion of the electronics, wherein the lateral axis is perpendicular to the longitudinal axis,
   wherein a center plane of the envelope extends along the longitudinal axis and extends parallel to the lateral axis, and
   wherein the rear portion has a thickness greater than X but no greater than 2X, and the front portion has a thickness no greater than X and is offset relative to the center plane of the envelope along a normal axis that extends perpendicularly from the center plane, whereby the liquid handling device can be assembled with another reversely oriented liquid handling device at a center-to-center spacing of X and a total combined width no greater than 2X.

2. The liquid handling device according to claim 1, wherein the barrel and motive device are disposed in a housing.

3. The liquid handing device according to claim 2, wherein the electronics are disposed in an electronics module removably mounted to the housing and contained with said envelope.

4. The liquid handling device according to claim 3, wherein the electronics module is disposed in the rear portion of the envelope.

5. The liquid handling device according to claim 3, wherein the electronics module and housing have respective plug-together mating connectors for electrically connecting the electronics module to electrical circuitry in the housing.

6. The liquid handling device according to claim 2, wherein the electronics include an onboard miniaturized electronic motor control with a communications input, the motor control being configured to mate with a communication module removably mounted to the housing and contained with said envelope.

7. The liquid handling device according to claim 6, further including:
   a gripper with contacts; and
   a docking station with contacts;
   wherein the housing includes contacts configured to mate with the contacts of the gripper and the contacts of the docking station, the gripper and/or the docking station allowing the device to operate aspirate or dispense sequences.

8. The liquid handling device according to claim 7, wherein the contacts on the gripper and docking station are electrically isolated and configured to provide power and communication signals to the device.

9. The liquid handling device according to claim 1, wherein the portion of the electronics is unitary with the housing.

10. A liquid handling system, including the liquid handling device according to claim 1; and
    the reversely oriented liquid handling device, wherein the liquid handling device and the reversely oriented liquid handling device include communication wires that are daisy chained to reduce wire count.

11. The liquid handling device according to claim 1, further including a valve contained within the envelope, and wherein the electronics control operation of the valve.

12. The liquid handling device according to claim 11, wherein the valve has a first port connected to a dispensing/aspirating lumen, in particular a syringe needle, a second port connected to the barrel, and a third port connected to an inlet that provides for connection of the liquid handling device to a source of or reservoir for a liquid.

13. The liquid handling device according to claim 11, wherein the valve has a first port connected to the barrel, a second port connected to a dispensing/aspirating lumen, in particular a syringe needle, and a third port connected to an inlet that provides for connection of the liquid handling device to a source of or reservoir for a liquid.

14. The liquid handling device according to claim 13, further including a user reagent addition pump that is coupled to the inlet by a supply line.

15. The liquid handling device according to claim 1, wherein the barrel is removably mounted to a housing of the liquid handling device contained within the envelope.

16. A liquid handling system including 2, 3, 4 or more of the liquid handling devices of claim 1 assembled in side-by-side relationship at a center-to-center spacing of X.

17. The liquid handling device according to claim 1, wherein X is 9 mm.

18. The liquid handling device according to claim 1, wherein X is 4.5 mm.

19. A liquid handling device according to claim 1, wherein the plunger is offset relative to the center plane of the envelope along the normal axis.

20. A liquid handling device according to claim 1, wherein the rear portion has a thickness, parallel to the normal axis, greater than X but no greater than 2X, and the front portion has a thickness, parallel to the normal axis, no greater than X and is offset relative to the center plane of the envelope along the normal axis that extends perpendicularly from the center plane.

* * * * *